US012564351B2

(12) United States Patent　　(10) Patent No.:　US 12,564,351 B2

Goldstein et al.　　(45) Date of Patent:　Mar. 3, 2026

---

(54) PERSONAL APPARATUS FOR CONDUCTING ELECTROENCEPHALOGRAPHY

(71) Applicant: BrainBit, Inc., New York, NY (US)

(72) Inventors: Boris Goldstein, New York, NY (US);
Vadim Sakharov, Taganrog (RU);
Sergey Bulanov, Taganrog (RU)

(73) Assignee: Brainbit, Inc., Rancho Santa Margarita, CA (US)

( * ) Notice: Subject to any disclaimer, the term of this patent is extended or adjusted under 35 U.S.C. 154(b) by 431 days.

(21) Appl. No.: 17/200,453

(22) Filed: Mar. 12, 2021

(65) Prior Publication Data

US 2021/0282695 A1　　Sep. 16, 2021

Related U.S. Application Data

(60) Provisional application No. 62/989,144, filed on Mar. 13, 2020.

(51) Int. Cl.
*A61B 5/384*　　(2021.01)
*A61B 5/00*　　(2006.01)
*A61B 5/256*　　(2021.01)
*A61B 5/263*　　(2021.01)

(52) U.S. Cl.
CPC .............. *A61B 5/384* (2021.01); *A61B 5/256* (2021.01); *A61B 5/263* (2021.01); *A61B 5/6814* (2013.01); *A61B 5/6831* (2013.01); *A61B 2560/0214* (2013.01)

(58) Field of Classification Search
CPC ......... A61B 5/369; A61B 5/256; A61B 5/263; A61B 5/6814; A61B 5/6831; A61B 2560/0214; A61B 2562/046
See application file for complete search history.

(56) References Cited

U.S. PATENT DOCUMENTS 8,897,852 B2 * 11/2014 Kato ..................... A61B 5/6831
600/509
2002/0188216 A1 * 12/2002 Kayyali ............... A61B 5/6814
600/544

(Continued)

OTHER PUBLICATIONS

"BrainBit"—4 channel EEG Headband", Jul. 15, 2018, https://web.archive.org/web/20180715001755/http://wiki.callibri.com/index.php?title=%22BrainBit%22 _-_ 4_channel_EEG_Headband [Retrieved on May 22, 2025] (Year: 2018).*

(Continued)

*Primary Examiner* — Rene T Towa
*Assistant Examiner* — Ari S Padda
(74) *Attorney, Agent, or Firm* — Khanh T. Glatzel, Esq.

(57)　　ABSTRACT

This invention discloses an apparatus for conducting electroencephalography while allowing for secure and easy application to a human subject's forehead. The apparatus may be changed in size to fit each human subject without affecting the electronic components within the apparatus. Operation of the apparatus may be by a computer programming product in the nature of a software on a computer or an application on a mobile computer device. Signals collected from the apparatus may be used in a variety of applications, including brain computer interface, transport safety, neurofeedback, esports, virtual and augmented reality, as well as tracking sleep patterns.

20 Claims, 6 Drawing Sheets

(56)  References Cited

U.S. PATENT DOCUMENTS

| 2009/0134887 | A1* | 5/2009 | Hu | A61B 5/6814 |
| | | | | 324/692 |
| 2012/0226127 | A1* | 9/2012 | Asjes | A61B 5/282 |
| | | | | 600/383 |
| 2015/0199010 | A1* | 7/2015 | Coleman | G06F 3/015 |
| | | | | 345/156 |
| 2015/0282760 | A1 | 10/2015 | Badower et al. | |
| 2015/0313496 | A1 | 11/2015 | Connor | |
| 2016/0140866 | A1* | 5/2016 | McGuire | A61B 5/6804 |
| | | | | 434/247 |
| 2016/0157777 | A1* | 6/2016 | Attal | A61B 5/291 |
| | | | | 600/383 |
| 2017/0119313 | A1* | 5/2017 | Helvick | A61B 5/02055 |
| 2018/0078206 | A1* | 3/2018 | Aimone | A61B 5/6831 |
| 2019/0200925 | A1* | 7/2019 | Aimone | A61B 5/0205 |
| 2021/0022636 | A1* | 1/2021 | Zhu | A61B 5/02055 |
| 2021/0085234 | A1* | 3/2021 | Hsu | A61B 5/4064 |

OTHER PUBLICATIONS

"Brainbit—4 channel EEG Headband—Neurotech Software Development Kit", May 30, 2018, XP093116053, URL: http://wiki.callibri.com/index.php?title=Brainbit_-_4_channel_EEG_Headband.

"Brainbit—4 channel EEG Headband—Neurotech Software Development Kit", Jul. 15, 2018, XP093116206, URL: https://web.archive.org/web/20180715001755/http://wiki.callibri.com/index.php?title="BrainBit-_4_channel_EEG_Headband.

"Brainbit User Manual—Neurotech Software Development Kit", Jul. 15, 2018, XP093116198, URL:https://web.archive.org/web/20180715034617/http://wiki.callibri.com/index.php?title=Brainbit_User_Manual.

"Brainbit Headband", Jan. 23, 2019, XP093116065, URL:https://www.youtube.com/watch?vSg1CWhDfpDE.

* cited by examiner

PERSONAL APPARATUS FOR CONDUCTING ELECTROENCEPHALOGRAPHY

BACKGROUND OF THE INVENTION

Field of the Invention

This invention relates to an apparatus used in electroencephalography. The apparatus can operate wirelessly and may be applied to a human subject's head in many settings with many practical applications.

Description of the Related Technology

Electroencephalography (EEG) is the recording of electrical signals along a mammal's scalp. Brains' neural activities generate electrical voltage fluctuations, whose signals may be measured by EEG. EEG measurements are useful for medical diagnosis and behavioral therapy. Other medical techniques involving the recording of bio-potential signals are electrocardiograms (ECG) and electromyograms (EMG).

Electroencephalography is particularly useful in diagnosis of conditions relating to brain injuries, such as seizure, stroke, brain tumors, Alzheimer's disease, or certain psychoses. Neural activities generate bio-potentials, which are collected by electrodes situated by a cap or by application of each electrode on certain head regions and conducted through electrical connections to a process hub.

EEG apparatuses have gone through evolution to become an integral part of modern applications, such as brain computer interface for controlling of electronic devices, neurofeedback activities, electronic sports (esports), health and wellness parameter collection, virtual and augmented reality, and to evaluate sleep pattern, among other applications.

EEG measurements typically require application of electrodes to the subject's head by either a cap application or placement of each electrode. Placement of each electrode is time consuming and requires a trained technician. Moreover, reusable caps and electrodes require cleaning and adding of gel, which may be time consuming and a means for germ transmission. An electrode cap and placement of each electrode for EEG measurement are both prone to recording incorrect signals with subject's movement. Traditional EEG apparatuses do not allow for strong movement by human subjects.

When EEG measurements are conducted using an electrode cap, customizing the electrode cap to fit users remain a challenge, due to various head sizes among humans. Disposable EEG caps propose an option to solve this problem, however disposable EEG caps can only be provided with pre-determined size.

Given the many challenges in conducting EEG, there remains a demand for size-adjustable EEG electrode placement means, where human subjects' comfort is maximized and bio-signals collected are of high quality. Customized computer software provided together with EEG equipment is also in high demand, such that EEG measurement can be conducted by non-medical personnel for applications other than medicine. The current invention seeks to solve these problems.

SUMMARY

According to embodiments of the present invention, there is provided an apparatus for performing electroencephalography on a human subject. The apparatus comprises a flexible, non-extendible ribbon wherein the electrodes, battery, and electronics are located, and a stretchable, elastic band covering the outside of the ribbon. The ribbon is divided into different segments to maximize comfort for the human subject wearing the apparatus, while also providing a way to ensure good contact and collection of bio-signals. The band provides a way to fit the various human subject's head sizes. The apparatus may further comprise a computer programming product, which can be customized by an end user to adapt the apparatus for use in different applications.

There is provided an apparatus for measuring electroencephalography, comprising:

a flexible ribbon with two ends having at least one signal electrode, a reference electrode, a common electrode, at least one battery, at least one electronic block, and multiple eyelets along the length of the ribbon;

a stretchable, elastic band mounted along the length of the ribbon through the multiple eyelets; and a detachable clasp configured to connect the two ends of the flexible ribbon and the band;

wherein the at least one electronic block is configured to collect bio-signals from the at least one signal electrode and electronically communicate collected bio-signals with an outside computing means, wherein the ribbon is divided into multiple segments, the segments being physically and operatively connected to each other, wherein each of the at least one battery and at least one electronic block is each located on a separate segment of the ribbon, and wherein the at least one signal electrode, the reference electrode, and the common electrode are located on one side of the ribbon while the multiple eyelets are on the other side of the ribbon.

There is provided an apparatus for measuring electroencephalography as above, wherein each of the at least one signal electrode is located on a separate segment of the ribbon.

There is provided an apparatus for measuring electroencephalography as above, wherein the at least one signal electrode comprises multiple spring loaded contact electrodes arranged in a grid, the contact electrodes are in electronic communication with the electronic block.

There is provided an apparatus for measuring electroencephalography as above, wherein the contact electrodes are gold plated.

There is provided an apparatus for measuring electroencephalography as above, wherein the at least one signal electrode comprises at least eight contact electrodes.

There is provided an apparatus for measuring electroencephalography as above, wherein the ribbon is made from pliable plastic.

There is provided an apparatus for measuring electroencephalography as above, wherein the band is made of cloth material.

There is provided an apparatus for measuring electroencephalography as above, wherein the electronic block and the battery are located on different segments, each of the segment contacts a human subject's the temple during use.

There is provided an apparatus for measuring electroencephalography as above, wherein the segments of the ribbon are operatively connected by flexible, electronically conductive wires.

There is provided an apparatus for measuring electroencephalography as above, wherein the common electrode and reference electrode are located on the same segment, the segment contacts the human subject's forehead during use.

There is provided an apparatus for measuring electroencephalography as above, wherein the common electrode, the reference electrode, and the signal electrodes are coated with the same conductive material.

There is provided an apparatus for measuring electroencephalography as above, wherein the at least one battery and the at least one electronic block are removable from the apparatus.

There is provided an apparatus for measuring electroencephalography as above, wherein the band's length is longer than the ribbon's length, and wherein the band loops through the clasp such that the effective working length of the band may be changed by adjusting the band's position relative to the clasp.

There is provided an apparatus for measuring electroencephalography as above, further comprising a computer programing product readable on a computing article.

There is provided an apparatus for measuring electroencephalography as above, wherein in the computer programming product is configured for additional configuration by an end user.

There is provided an apparatus for measuring electroencephalography as above, wherein the computer programming product is capable of being configured to filter raw data collected by the apparatus, identify areas of artifact, and provide signal spectrum composition.

There is provided an apparatus for measuring electroencephalography as above, wherein the computer programming product is capable of being further configured to identify a human subject's neural activity condition.

There is provided a method to measure electroencephalography, comprising: providing an apparatus comprising:

a flexible ribbon with two ends having at least one signal electrode, a reference electrode, a common electrode, at least one battery, at least one electronic block, and multiple eyelets along the length of the ribbon;

a stretchable, elastic band mounted along the length of the ribbon through the multiple eyelets; and a detachable clasp configured to connect the two ends of the flexible ribbon and the band;

wherein the at least one electronic block is configured to collect bio-signals from the at least one signal electrode and electronically communicate collected bio-signals with an outside computing means, wherein the ribbon is divided into multiple segments, the segments being physically and operatively connected to each other, wherein each of the at least one battery and at least one electronic block is each located on a separate segment of the ribbon, and wherein the at least one signal electrode, the reference electrode, and the common electrode are located on one side of the ribbon while the multiple eyelets are on the other side of the ribbon;

providing a power source to the apparatus;

placing the apparatus onto a human subject's head such that the segment having the common electrode and the reference electrode comes into physical contact with the human subject's forehead;

providing an outside computing device, the outside computing device having an interface and a computer programming product configured to operatively connect to the apparatus;

tightening the stretchable, elastic band using the clasp to secure the apparatus on the human subject's head;

activating the apparatus using an outside computing means interface; and collecting bio-signals from the human subject using the outside computing means interface.

There is provided a method to measure electroencephalography as above, further comprising analyzing the collected bio-signal using the computer programming product and outputting at least one output.

ABBREVIATIONS

DVD: Digital Versatile Disk
EEG: Electroencephalography
EMG: Electromyograms
ECG: Electrocardiograms
mm: millimeters
PCBA: Printed Circuit Board Assembly
USB: Universal Serial Bus

DETAILED DESCRIPTION OF CERTAIN INVENTIVE EMBODIMENTS

Figure 1:
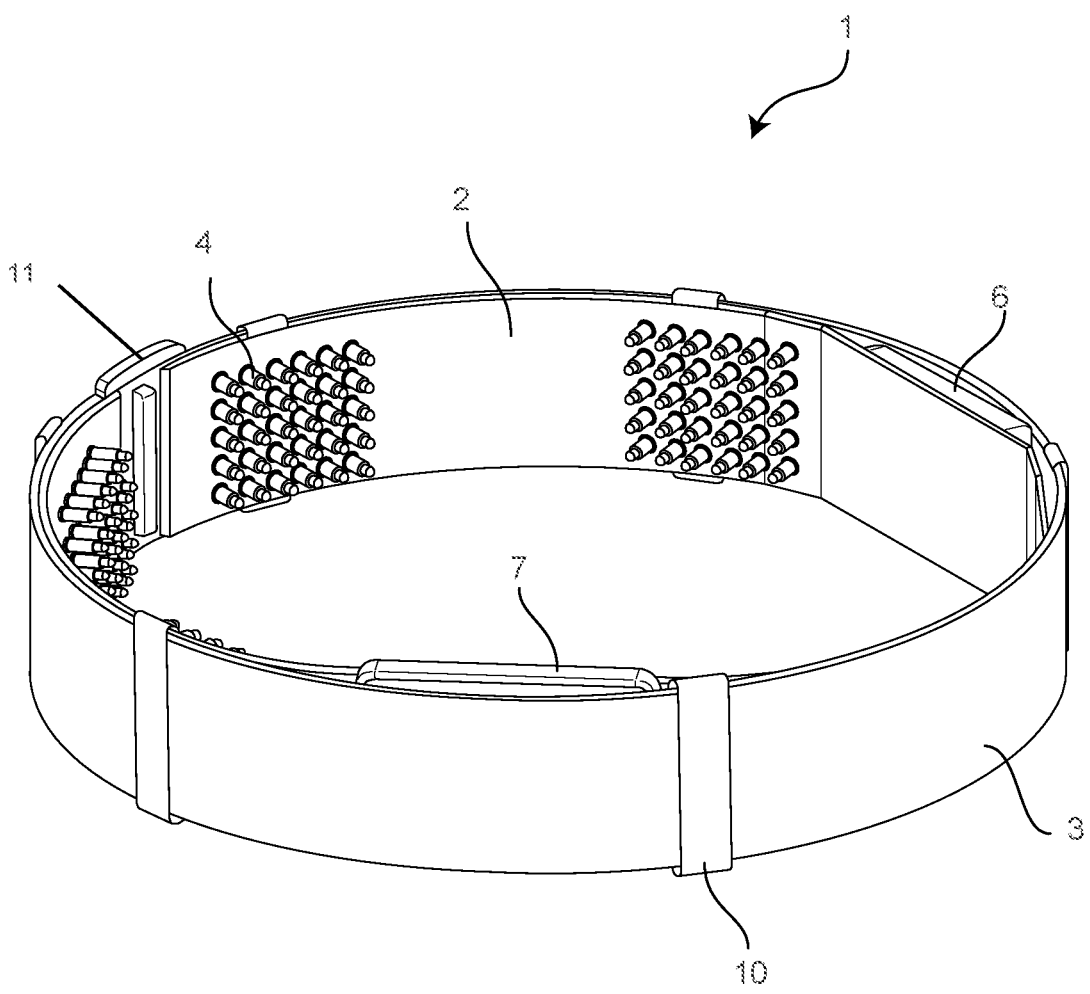
FIG. 1 depicts a perspective view of the EEG apparatus according to an embodiment.

This present invention is capable of being embodied in various forms. The description below of several embodiments is made with the understanding that the present disclosure is to be considered as an exemplification of the claimed subject matter and is not intended to limit the attached claims to the specific embodiments illustrated. The headings used throughout this disclosure are provided for convenience only and are not to be construed to limit the claims in any way. Embodiments illustrated under any heading may be combined with embodiments illustrated under any other heading.

As used herein, the verb "to comprise" in this description, claims, and other conjugations are used in its non-limiting sense to mean those items following the word are included, but items not specifically mentioned are not excluded.

Reference to an element by the indefinite article "a" or "an" does not exclude the possibility that more than one of the elements are present, unless the context clearly requires that there is one and only one of the elements. The indefinite article "a" or "an" thus usually means "at least one." Additionally, the words "a" and "an" when used in the present document in concert with the words "comprising" or "containing" denote "one or more".

As used herein in the specification and claims, including as used in the examples and unless otherwise expressly specified, all numbers may be read as if by prefaced by the word "about" or "approximately", even if the term does not expressly appear. The phrase "about" or "approximately" may be used when describing magnitude and/or position to indicate that the value and/or position described is within a reasonably expected range of values and/or positions.

All dimensions given herein are for illustrative purposes only and in no way will limit the inventions by these dimensions. It is to be understood that the invention may be constructed to have different dimensions than those provided herein and is still within the scope of the embodiments described herein. Drawings are not necessarily drawn to scale.

As used herein, like numerals indicate like components even though the components may be used in different manners or at different places. Where there are multiple components of the same nature, a numeral refers to one, some, or all of the components of the same nature, depending on the context.

All dimensions specified in this specification are by way of example only and not intended to be limiting. The actual size of the EEG apparatus herein may be chosen or modified for intended use, including use in adults with different head sizes, in children and/or infants. The actual size may also be tailored to the specific human subject who may use this EEG apparatus. Other sizes and dimensions are contemplated.

As used herein, the term "ribbon" refers to a swath of material having a length that is substantially longer than the width and a small thickness, the ribbon has multiple segments with components embedded into or attached to it.

As used herein, the term "flexible" means the ability to be changed in shape by a physical force and then return back to that shape once the physical force is removed.

The terms "human subject" and "subject" are used interchangeably to refer to a human whose head is affixed with the EEG apparatus described herein during use.

As used herein, the term "bio-signal" refers to bioelectrical signals that may be measured.

As used herein, the term "outside computing means" or "outside computing device" refers to a computing article not physically connected to the EEG apparatus as disclosed herein and can operate independently from the EEG apparatus.

As used herein, the International Standard electrode placement system, or the 10-20 system refers to the International 10-20 system to describe and apply the location of scalp electrodes in the context of an EEG test or experiment.

The EEG apparatus disclosed herein and its components may be made of any suitable material for the intended purpose of the electroencephalography apparatus. Specific materials may be discussed herein but only for illustration purposes only and will not be understood as limiting in anyway.

The EEG apparatus according to embodiments collects human subjects' bio-signal from their brain activity, which may be displayed as an output and interpreted. The EEG apparatus disclosed herein may be easily stored and transported and therefore is suitable for use both in clinic settings and at non-clinical settings, such as in battlefields, accident scenes, or in entertainment. The EEG apparatus may be used for medical treatment and research purposes or other purposes, such as training, meditation, sleep studies, or esports. Other uses may be possible, depending on the need determined by users.

Embodiments of this invention relate to an EEG measurement apparatus to be worn on the head by a human subject during measurement. The EEG apparatus' size may be changed by operation of a clasp to fit different subject head sizes.

FIG. 1 is a perspective view of the apparatus 1 completely assembled. The apparatus comprises two parts, a flexible, inextensible ribbon 2 having operational parts and a stretchable, elastic band 3 covering the outside of the ribbon 2. Both the ribbon 2 and the band 2 may have two (2) ends and may be in the form of a head band, which may be wrapped around a human's head. The elastic band 3 may not have any electronically operable parts but may serve as a means to change the apparatus' 1 length when necessary and to exert pressure on a subject's skull during use and keep the apparatus 1 in place. By way of illustration, the apparatus 1 may be about 46-53 centimeters in length and about 2.5-3.5 centimeters in width.

The elastic band's length may be longer than the ribbon's length, such that the elastic band 3 may loop around the ribbon 2 by resting in the eyelets. Tightening or loosening of the elastic band 3 using the clasp 11 may change the effective working length of the band 3 and affect the position of the various components present on the ribbon 2 upon application to the subject's head.

In FIG. 1, the electronic block 6 and the battery block 7 are shown in a position on the outside of the ribbon 2. This arrangement is an option, other arrangements may be present depending on the need. Specifically, the electronic block 6 and the battery block 7 may be both on the outside or on the inside of the ribbon 2, or the electronic block 6 may be on the inside while the battery block 7 may be on the outside, or vice versa.

Figure 2:
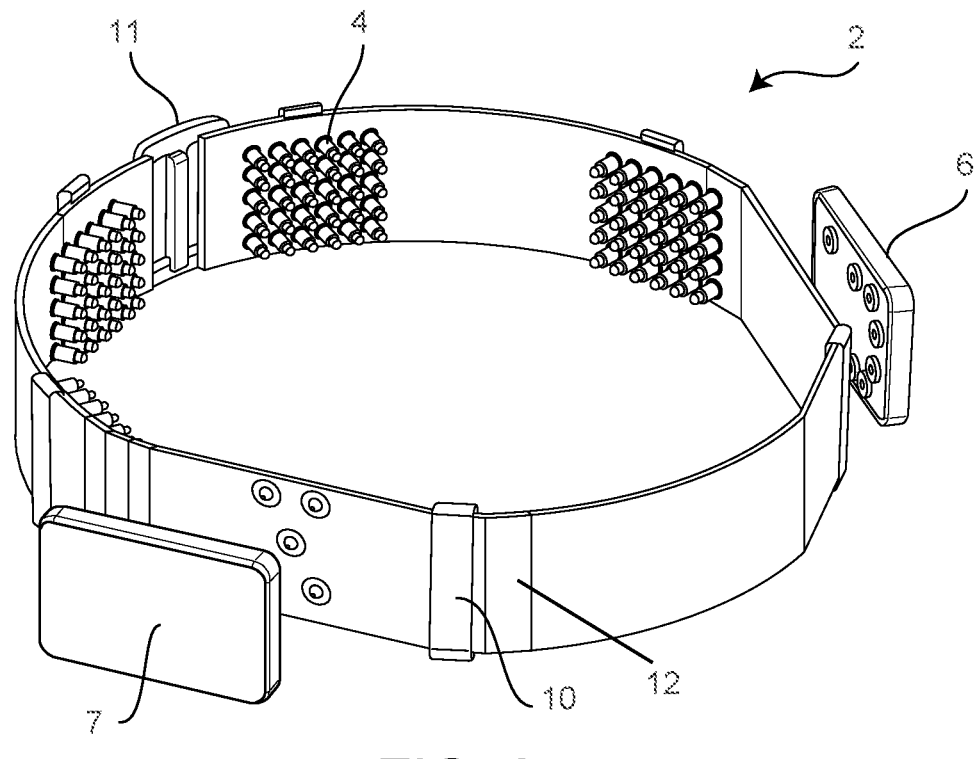
FIG. 2 depicts a perspective view of the ribbon within the EEG apparatus with the battery and the electronic block detached from the ribbon.

FIG. 2 is a perspective view of the ribbon 2 with the battery 7 and the electronic block detached from the ribbon 2. In this embodiment, the battery 7 and the electronic block 6 are both situated on the outside of the ribbon 2 when attached. The ribbon 2 may be a swath of flexible, inextensible material, which may be pliable plastic or polymer divided into multiple segments. Each of the segment may be connected to another segment by a connecting mechanism 12, allowing the ribbon 2 to wrap around the human subject's head during use while maintaining a sturdy body for attaching electrodes, batteries, electronics, and other components. There may be eyelets 10 situated on the outside surface of the ribbon 2, such that the eyelet 10 body extends away from and does not contact the human subject's head during measurement of EEG signal. FIG. 2 shows a ribbon 2 with seven segments but the number of segments may be higher or lower.

In embodiments, the ribbon 2 may be coated with silicone to prevent dust and moisture accumulation on the apparatus 1. The ribbon 2 as a whole may be dust and moisture resistant, such that it can be rinsed with running water without compromising the ribbon's structure or operational integrity. The ribbon 2 may have substantially the same width throughout, or alternatively with narrowing width at the edges of the forehead. The narrowing may allow the ribbon 2 to better adjust to subjects with receding types of foreheads. The ribbon 2 may be manufactured by silicone molding under pressure. Segments of the ribbon 2 may be operatively and electrically connected using flexible, electronically conductive wires. The segments may also be operatively and electrically connected by printed circuitry.

Figure 3:
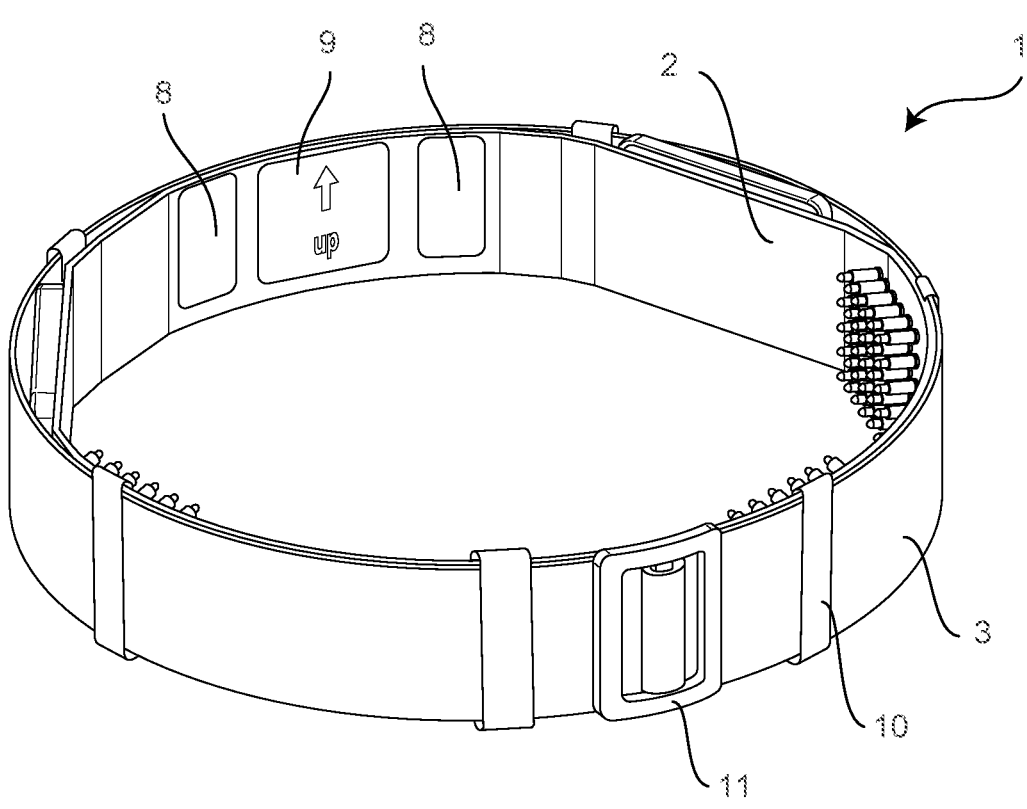
FIG. 3 depicts another perspective view of the EEG apparatus wherein the reference electrodes can be seen.

FIG. 3 illustrates another perspective view of the EEG apparatus 1 according to embodiments. In FIG. 3, the segment having the reference electrode 9 and common electrodes 8 are shown. The reference electrode 9 as shown in FIG. 3 has an arrow with the word "up" to assist with orienting the apparatus 1 during application to a subject's head. Both the reference electrode 9 and common electrodes 8 may be generally flat and come into contact with the subject's forehead during use and may be coated with the same conductive material, such as gold or silver chloride. Other coating materials may be suitable. The reference electrode 9 and common electrodes 8 may be electrically and operationally connected to other electrodes, the electronic block 6, and/or the battery 7 by wired connections, such as printed circuits. Other connection means and methods are contemplated.

Figure 4:
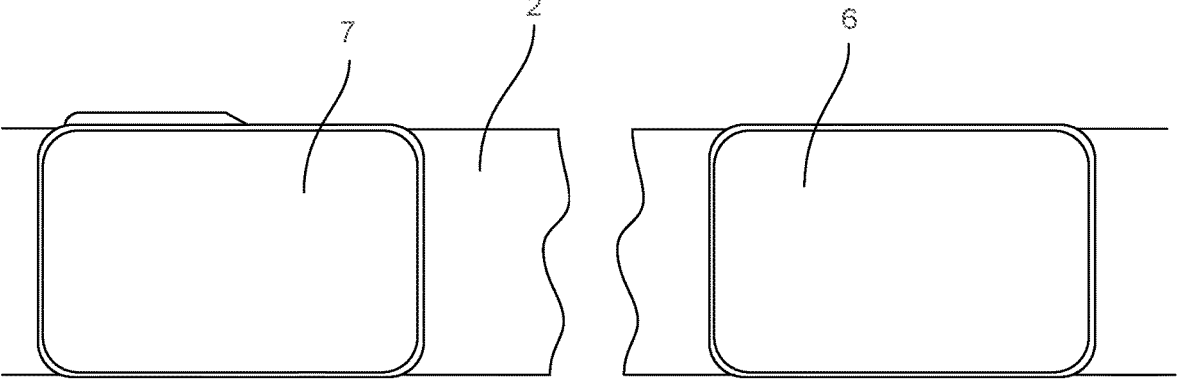
FIG. 4 is the top view of a battery and an electronic block as assembled into the ribbon.

In embodiments, one of the segments may house an electronic block 6. FIG. 4 illustrates the top view of the electronic block 6 together with the battery 7. The electronic block 6 may comprise a housing, which may contain electronic circuit and other electronic means to collect biosignals from neural activities. The electronic block 6 may be shaped to fit with the length of the segment which it is attached to. The thickness of the electronic block 6 may be small, such that an elastic band may be attached to the ribbon 6 and cover the electronic block 6 without a clunky appearance. The electronic block 6 may be removable from the ribbon 2. Attached of the electronic block 6 to the ribbon may be by snapped on button, as shown in FIG. 2, by gel, Velcro, or other suitable attachment means.

The electronics inside the electronic block 6 may be a flexible printed circuit board with necessary components for the operation of the EEG apparatus 1, such as Bluetooth module, analog frontend chip, analog-digital chip, and microprocessor, among other components. The electronic block 6 may be electrically connected to the electrodes 5, 8, 9 and the battery 7 via electrical connections, which may be printed circuits. Other wired connection means are contemplated.

The electronic block 6 may comprise means to collect bio-signals from the electrodes 5, 8, 9, filter and preliminarily analyze collected signal, then communicate with outside computing means, such as a computer, a desktop, a laptop, a smart phone, a tablet, or a computer embedded into another device. Communication with outside computing means may be by wireless communication means, such as by Bluetooth communication. Other wireless communication means are contemplated. Communication with outside computing means may also be by wired connection.

In embodiments, another segment within the ribbon 6 may house a battery 7. There may be at least one battery 7 present in the apparatus 1, but more than one battery is contemplated. The battery 7 may be attached to a segment of the ribbon 7 such that the battery 7 is on the non-skin-contact side of the ribbon 2. FIG. 4 illustrates the top view of the battery 7 as assembled into the ribbon 2. The battery 7 may be removable. The apparatus 1 may remain in hibernation mode when not in used with the battery 7 attached to the apparatus 1 and the battery 7 may be removed for charging when needed. In an alternative embodiment, the battery 7 may be permanently built into the ribbon 2 and is chargeable. In yet another alternative embodiment, the apparatus 1 may be powered by non-battery means, such as by an electrical plug connected to a power point. The apparatus 1 may be also be provided with both power supply means, i.e.

with a battery and an electrical plug. Optionally, an on/off button may be included if the battery 7 is built into the apparatus 1.

In embodiments, the segment carrying the battery 7 and the segment carrying the electronic block 6 may be positioned such that each of these segments may touch the human subject's temple during use of the apparatus 1. The human temple is relatively flat, allowing the electronic block 6 segment and the battery 7 segment to come into contact with the human head without causing discomfort to the human subject.

Figure 5:
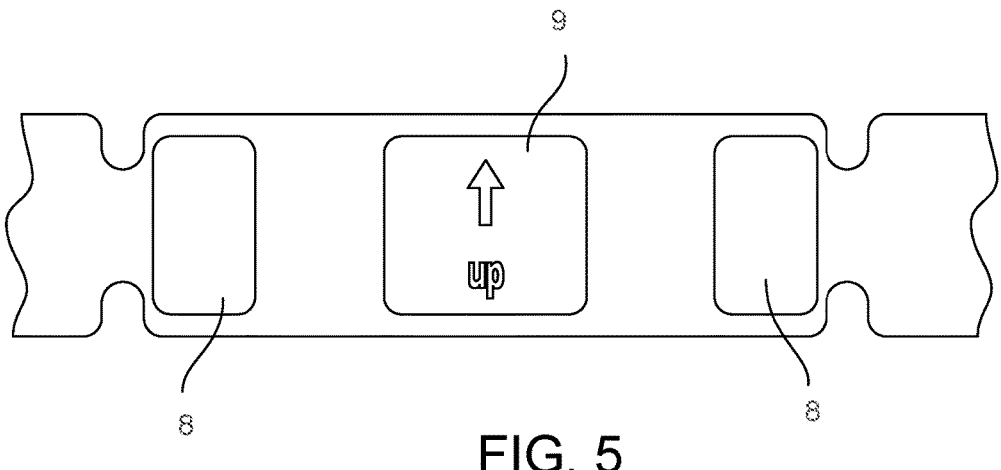
FIG. 5 is the front view of the common electrode and the reference electrode.

In embodiments, between the battery 7 segment and the electronic block 6 segment may be a reference segment. On the inside of the reference segment may be a common electrode for grounding 8 and a reference electrode 9. FIG. 5 shows the common electrode 8 and the reference electrode 9 as present on the inside of the reference segment. This same segment is also visualized on FIG. 3. The reference segment may be located and sized to fit with the forehead region of the human subject. Both the common electrode 8 and the reference electrode 9 may be coated in the same material with the electrodes 4, preferably with gold. By coating the electrodes with the same material, electro-galvanic effects are minimized, thereby improving durability and signal quality. The flat electrodes on the forehead region also may improve signal quality. Sweat may gather between the flat electrodes and the human skin on the forehead, thereby increasing conductivity and consequently, signal quality.

The common electrode 8 and the reference electrode 9 may be generally flat, such that the electrodes are flexible enough to fit the curve of the skull while maintaining contact with the forehead. Since the forehead is hairless, electrodes on this segment may be flat to improve comfort and at the same time flexible enough to maintain contact around the forehead's curvature.

As shown in FIG. 5, the common electrode 8 may be split into two (2) parts, with the reference (signal) electrode 9 situated between the two parts. The two-part common electrode 8 may increase contact surface area with the subject's forehead. In the apparatus 1, the two-part common electrode is the connector in a single circuit by wire on the flexible, inextensible ribbon 2.

In an alternatively embodiment, the reference segment may be made from silicone molding such that the shape fits the curve of the forehead. This may improve contact between the electrodes and the subject's forehead. In this embodiment, the reference segment may have a different inside surface than the other segments, in that it has been molded to fit the forehead and is not generally flat on the inside.

In embodiments, on the remaining segments of the ribbon 2 may be signal electrodes 4. Signal electrodes 4 may collect bio-signals from brain activities and transmit collected signals to the electronic block 6 through wired connection. Signal electrodes 4 may collect bio-signals using direct, physical contact with the skin on the skull. However, the skull is covered in hair and thus signal electrodes may need to ensure an adequate contact surface between the electrode head and the subject's scalp.

Figure 6:
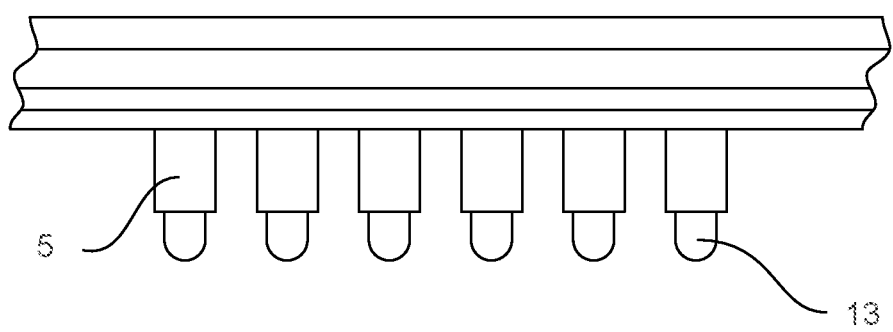
FIG. 6 is the front view of the contact electrodes on the EEG apparatus according to embodiments.
Figure 9:
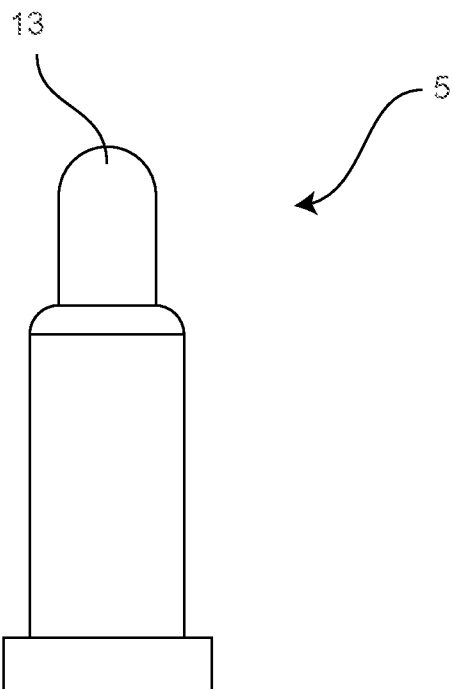
FIG. 9 is the front view of a single contact electrode in the EEG apparatus according to embodiments.

In embodiments, signal electrodes 4 may comprise multiple contact electrodes 5 in the nature of spring-loaded pins with contact heads 13. FIG. 6 illustrates the contact electrodes 5 in a row, while FIG. 9 illustrates an isolated contact electrode 5. Each of the contact heads 13 may comprise a rounded half-ball, in the shape of a hemisphere connected to a spring (not shown), which may be housed inside a substantially tubular body similar to a pin, and the tubular body may rest on a base which is soldered to the printed circuit board that forms the wired connection among the electrical components on the ribbon 2. The contact head 13, the spring, and the tubular body together form a contact electrode 5. The pin-like shape of the contact electrodes may allow for penetration through hair and increase the ability to form a good contact with the scalp, thereby increasing signal quality.

The contact electrodes 5 may be gold plated or coated with other coating materials, such as silver alloys (silver and silver chloride). Gold coating, however, may minimize standard electrode potential, thereby ensuring high quality signal upon contact with the subject's skin. Coating materials for contact electrodes 5, common electrode 8, and the reference electrode 9 may be the same, such that electro-galvanic effects may be minimized. Contact electrodes 5 may be made of conductive materials, such as copper or brass. By way of example, each contact electrode 5 measures at 7.2 mm in length, the head is 2 mm in diameter and 2.2 mm in length, and the tubular body is 5 mm in length and 3 mm in diameter, and the base is 3.5 mm in width. These dimensions are only for illustrative purposes and shall not limit this invention in anyway.

Contact electrodes 5 may be provided in varying lengths to suit various users. By way of an example, contact electrodes 5 with long pins may provide better penetration through a human subject's curly, thick hair. On the other hand, infants, toddlers, or bald human subjects may use contact electrodes 5 with shorter pins. Contact electrodes 5 may be provided affixed to the EEG apparatus 1 or may be provided separately. In that case, prior to use, contact electrodes 5 may be attached to the apparatus 1 at appropriate locations. This embodiment may allow the apparatus 1 to be provided with various contact electrodes 5 with varying length and the user may choose the appropriate contact electrodes 5 for each human subject.

In another embodiment, contact electrodes 5 may be provided separately from the apparatus 1. In this embodiment, the ribbon 2 may have premade attachment points and mechanisms to allow attaching of contact electrodes 5 to the ribbon 2 by a user. For example, a segment where contact electrodes 5 may be assembled into may be configured such that it may be detached from the ribbon 2. Holes and/or snap on buttons may be available on that segment to allow contact electrodes 5 to be assembled into. Thereafter the segment may be re-attached into the ribbon 2. In yet other embodiments, segments of the ribbon may be provided separately and may be assembled together prior to use. The design may need to enable electrical contact between the segments upon assembly to enable functioning of the apparatus 1 as a whole.

Figure 7:
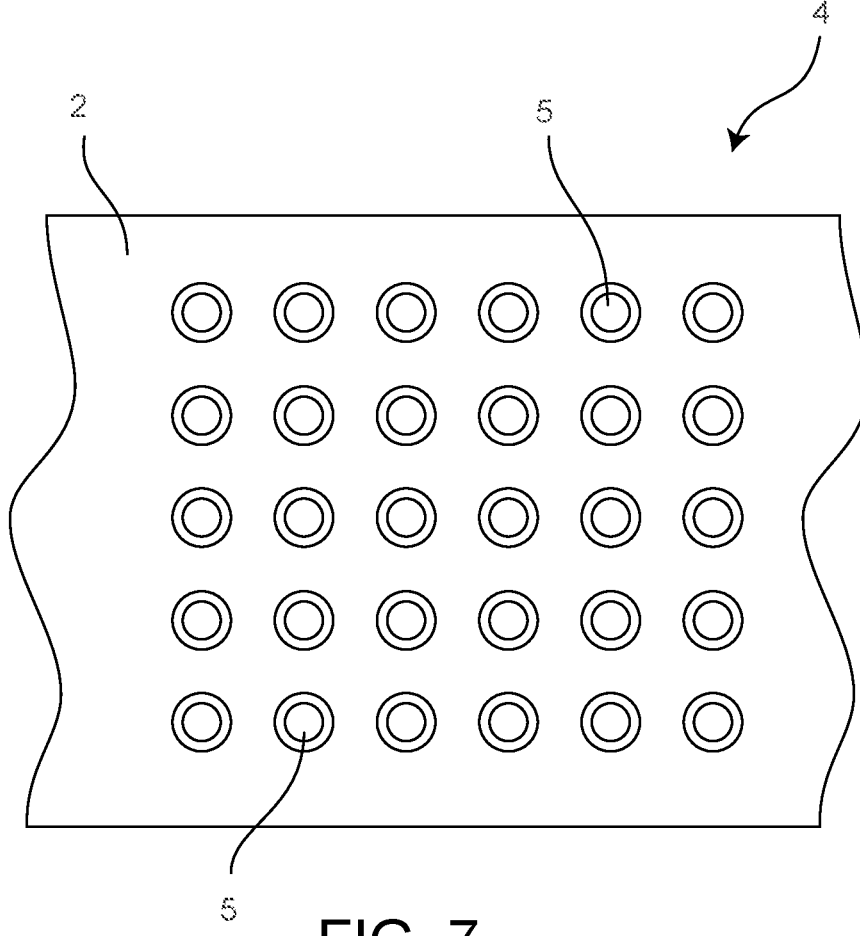
FIG. 7 is the top view of the contact electrodes of the EEG apparatus according to embodiments.
Figure 8:
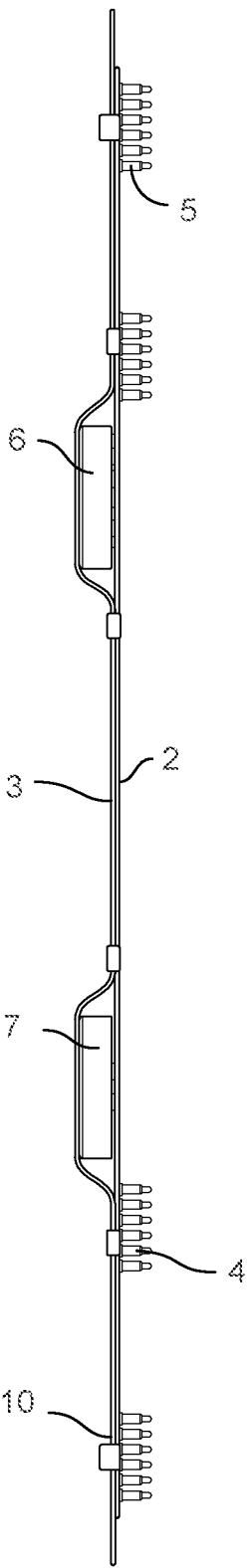
FIG. 8 is the cross sectional view of a section of the EEG apparatus according to embodiments, taken along the length of the ribbon and the elastic band.

FIG. 7 illustrates a top view of a signal electrode 4 according to embodiments. Signal electrodes 4 may be formed by multiple contact electrodes 5 arranged into an array. By way of example, FIG. 7 shows contact electrodes 5 arranged into a grid of five by six (5×6) contacts, equaling thirty (30) contact electrodes 5 in total. Other amounts of contact electrodes 5 and other arrangements are contemplated. A large amount of contact electrodes 5 may increase the probability of obtaining good quality EEG signal. By way of an example, the contact electrodes 5 may take up an area of about 1.8 to 2.5 square centimeters on the ribbon 2. The contact electrodes 5 may take up different sizes of area, depending on how many contact electrodes 5 and the size of the electrodes.

In embodiments, contact electrodes 5 may be located on a flexible substrate surface, which may increase conductivity and improve signal collection from contact electrodes 5. The ribbon 2 may have a flexible printed circuit with substrate surface and contact electrodes 5 are soldered onto the printed circuit. Additional cushion material may be added on the ribbon 2 at the location with contact electrodes 5 to lessen the pressure exerted onto the electrodes 5 when the apparatus 1 is affixed to the subject's head.

Upon applying the apparatus 1 to a subject's head, the signal electrodes 4 may be placed such that two are on the temporal lobe regions corresponding to the T3 and T4 positions according to the International 10-20 electrode system and two are on the occipital lobe regions corresponding to the O1 and O2 positions according to the International 10-20 electrode system, and the reference electrode 9 and common electrodes 8 are on the forehead.

In embodiments, the electrodes 5, 8, 9, the battery 7, and the electronic block 6 may be in electrical communication with each other via a wired network embedded in the ribbon 2, such as by printed silver chloride connection or by conductive wires. A printed circuit board may also be provided with an electronic block.

In embodiments, the ribbon 2 may have a clasp 11, which may be located between two (2) segments, such that the clasp 11 fits around the nape of the subject's head during use. The clasp 11 may be detachable from the ribbon 2 and the band 3. Fitting the apparatus 1 with the clasp 11 fitted lower on the subject's skull may increase comfort for the subject during use. The clasp 11 may be as narrow as possible to allow the apparatus 1 to fit on small human head sizes. The clasp 11 may also be where the elastic band 3 may loop through. The clasp 11 is shown in FIG. 1 at the connection between two segments carrying contact electrodes.

In embodiments, the apparatus 1 may have an elastic, stretchable band 3 looping through the eyelets 10 and covering the outside wall of the ribbon 2. The elastic band 3 may be made of, for example, elastic plastic or stretchable cloth. The elastic band 3 may loop through the eyelets 10 and the clasp 11, and slide freely along the inextensible ribbon 2. FIG. 1 and FIG. 3 both show the band 3 looping through the eyelets 10 on the non-skin contact side of the ribbon. During use, the elastic band 3 may exert pressure in a stretching position onto the human subject's skull, thereby holding the apparatus 1 in place, preventing movement of the components on the ribbon 2, and facilitating reduction of artifacts in collected signals. The elastic band 3 may have considerable maximum length under stretched condition, such that during wear, relatively little stretching is required and pressure on the skull does not increase significantly in human subjects with larger head sizes. The clasp 11 may be used to extend the working length of the elastic band 3, such that the apparatus 1 as a whole may be extended to fit the subject's head size.

In embodiments, the apparatus 1 may further comprise a computer programming product readable on a computing article. This computer programming product may be configured for various applications, such as for brain computer interface, transportation safety, meditation, esports, neuro-feedback, virtual and augmented reality, or for monitoring of sleep patterns. The computer programming product may be provide as a software development kit, such that it may be further configured by an end user for specific applications of the apparatus.

In embodiments, the computer programming product may be provided as a software development kit with three levels for development. The first level may provide the ability to customize for filtering raw EEG data to separate any frequency rhythms, develop algorithms to identify areas of artifacts in EEG data, as well as signal spectrum composition. The second level of the software development kit may be developed to help identify a subject's condition by analyzing their frequency rhythms, thereby identifying various states or neural activity condition, such as relaxation, deep relaxation, normal activity, agitation, or strong agitation. The third level of the software development kit may be developed to provide a more in-depth assessment of a subject's various states during specific activities, such as meditation depth, relaxation level, or emotion detection.

The computer programming product may be a software operable on a computer or an application operable on a mobile computing device such as a smart phone or a tablet. The computer programming product may be configured to wirelessly connect with and activate the EEG apparatus. During the EEG apparatus' operation, the computer programming product may collect signals from the EEG apparatus, process data received, and output certain data and/or graph for viewing by users. Results collected from the EEG apparatus may have many applications, such as medical diagnosis, transportation safety, neurofeedback, meditation monitoring, sleep monitoring, esports, research, virtual and augmented reality, etc.

Using the Apparatus

In use of the apparatus, the apparatus may be provided completely assembled, with a battery and/or electrical plug as a power source in place. The device may be fitted onto the human subject's head, such that the segment with the common and reference electrode comes into contact with a human subject's forehead. The elastic band may stretch to fit the apparatus around the circumference of the human subject's skull. Some hair parting may be required to improve contact between the electrode head and the scalp.

If the apparatus is provided with the contact electrodes not yet affixed in place, a user may affix the contact electrodes to the specific attachment points on the signal electrodes. Once affixed in place, the contact electrodes should be checked for stability and secured in place prior to applying to a human subject's head. A battery, if not already affixed in place, may be added to the apparatus.

Hair parting may be necessary to ensure good contact between the contact head on the contact electrodes and the subject's scalp. Careful placement to ensure the reference electrode and the common electrode are placed at the forehead region is required. Once the apparatus is in place, the elastic band may be tightened and locked using the clasp. The apparatus is now securely affixed to the human subject's head.

Once affixed to human subject's head, the apparatus may be turned on by pressing the on/off button, or it may be already on hibernation mode and only needs activation by an outside computing means embedded with a computer programming product configured to operate the apparatus. The remote computing means should be activated and the computer programming product also in operating mode. Once the apparatus is in operating mode, the remote computing means may activate the apparatus by means of the computing programming product. Contact electrodes touching the human subject's scalp may collect bio-signals from the human subject. Collected signals may be transmitted through wired connection between the contact electrodes and the electronic block.

The electronic block may receive signals from the various electrodes, filter raw signal and/or preliminarily analyze collected signals. Data may then be transmitted via wireless communication between the electronic block and the remote computing means using Bluetooth communication. Using the computer programming product, the user may analyze collected data and use the results in multiple applications. The computer programming product may output certain displays from the collected bio-signals, including, but not limited to, graphical representations, models, numerical values, or images. Signals collected from the apparatus may be used in a variety of applications, including brain computer interface, transport safety, neurofeedback, esports, virtual and augmented reality, as well as tracking sleep patterns.

Removal, Cleaning and Storage of the Apparatus

After use, the apparatus may be removed from the subject's head by loosening the ribbon at the clasp, thereby reducing the pressure exerted onto the subject's head. The apparatus may be lifted off from the subject's head once a physical gap appears between the apparatus and the subject's head or once the upward movement of the apparatus may be effectuated without exerting pain to the subject. Thereafter the apparatus may be cleaned and/or stored for future use.

Cleaning of the apparatus may be by rubbing alcohol wipes or other antibacterial wipes on the inner surface of the apparatus, where contact between the apparatus and the subject's head occurs. Cleaning by rinsing with running water is also an option. Since the electrodes are dry electrodes, the contact heads may be cleaned using wipes and then left to dry without affecting functionality. The apparatus may be stored in a dry, cool place for use on the same subject and/or on another subject in need thereof.

Construction of the Apparatus

The device may be constructed of available off-the-shelf components and custom made parts. Off-the-shelf components include microprocessor PCBA (Printed Circuit Board Assembly), battery charging and load sharing PCBA, battery, switch buttons, various basic PCBA components, connectors, H-bridge controller, inductors, capacitors, resistors, wires, fasteners, etc. Custom parts include injection-molded plastic parts forming the ribbon, printed circuit board embedded therein, electrodes printed or soldered thereon, and the elastic band.

The ribbon may be made from silicone adhesive tape, in particular kSil GP40 PSA SE plastic parts by kSil Silicone Engineering Ltd. with the based material being polyurethane. The band may be made from polyester fiber braided latex thread. The clasp may be made from plastic such as polypropylene. The eyelets may be made from the same material with the band or from a different material, such as polypropylene. Other suitable materials may be used.

The computer programming product is custom made to accompany the apparatus and is provided in a physical medium such as a USB drive, a memory card, or a DVD disk. Alternatively, the computer programming product may be made available for download from the Cloud by the user as an application on a mobile device or a software on a computing device.

Parts may be assembled by hand and/or by automated means. Parts that are connected to each other are done so using any combination of the conventional mechanical fastening techniques (e.g., screws, pins, etc.) or by molding and/or soldering. PCBAs are constructed per typical commercial manufacturing methods. Operations such as soldering are conventionally performed using standard tools.

While the present invention has been discussed in detail with reference to certain embodiments, other embodiments are possible. Therefore, the scope of the appended claims should not be limited to the description of the preferred embodiments contained in this disclosure.

All references, including publications, patent applications, and patents cited herein are hereby incorporated by reference to the same extent as if each reference were individually and specifically indicated to be incorporated by reference and were set forth in its entirety herein. It will be readily apparent to those skilled in the art that a number of modifications and changes may be made without departing from the spirit and the scope of the present invention. It is to be understood that any ranges, ratios, and range of ratios that can be derived from any of the data disclosed herein represent further embodiments of the present disclosure and are included as part of the disclosure as though they were explicitly set forth. This includes ranges that can be formed that do or do not include a finite upper and/or lower boundary. Accordingly, a person of ordinary skill in the art will appreciate that such values are unambiguously derivative from the data presented herein.

What is claimed is:

1. An apparatus for measuring electroencephalography, comprising:
   a flexible, inextensible ribbon with two ends having at least one signal electrode, a reference electrode, a common electrode, at least one battery, at least one electronic block, and multiple eyelets along the length of the ribbon;
   a stretchable, elastic band mounted along the length of the ribbon through the multiple eyelets; and
   a detachable clasp configured to connect the two ends of the flexible ribbon and the stretchable, elastic band;
   wherein the at least one electronic block is configured to collect bio-signals from the at least one signal electrode and electronically communicate collected bio-signals with an outside computing means,
   wherein the ribbon is divided into multiple segments along the length of the ribbon, the segments being physically and operatively connected to each other,
   wherein each of the at least one battery and at least one electronic block is each located on a separate segment of the ribbon,
   wherein the at least one signal electrode, the reference electrode, and the common electrode are located on one side of the ribbon while the multiple eyelets are on the other side of the ribbon,
   wherein each of the segments is connected to another segment by a connecting mechanism and the connecting mechanism is detachable from the segments,
   wherein the common electrode is split into two parts, and the reference electrode is situated between the two parts of the common electrode,
   wherein the two-part common electrode and the reference electrode are situated on a reference segment, and
   wherein the reference segment has silicone molding on the inside surface to fit the curve of the forehead.

2. The apparatus of claim 1, wherein each of the at least one signal electrode is located on a separate segment of the ribbon.

3. The apparatus of claim 1, wherein the at least one signal electrode comprises multiple spring-loaded contact electrodes arranged in a grid, the contact electrodes are in electronic communication with the electronic block.

4. The apparatus of claim 3, wherein the contact electrodes are gold plated.

5. The apparatus of claim 3, wherein the at least one signal electrode comprises at least eight contact electrodes.

6. The apparatus of claim 1, wherein the contact electrodes are detachable from the ribbon.

7. The apparatus of claim 1, wherein the ribbon is made from pliable plastic.

8. The apparatus of claim 1, wherein the stretchable, elastic band is made of cloth material.

9. The apparatus of claim 1, wherein the electronic block and the battery are located on different segments, each of the segments contacts a human subject's temple during use.

10. The apparatus of claim 1, wherein the segments of the ribbon are operatively connected by flexible, electronically conductive wires.

11. The apparatus of claim 1, wherein the common electrode and reference electrode are located on the same segment, the segment contacts the human subject's forehead during use.

12. The apparatus of claim 1, wherein the common electrode, the reference electrode, and the signal electrodes are coated with the same conductive material.

13. The apparatus of claim 1, wherein the at least one battery and the at least one electronic block are removable from the apparatus.

14. The apparatus of claim 1, wherein the stretchable, elastic band's length is longer than the ribbon's length, and wherein the stretchable, elastic band loops through the clasp such that the effective working length of the stretchable, elastic band may be changed by adjusting the stretchable, elastic band's position relative to the clasp.

15. The apparatus of claim 14, further comprising a computer programing product readable on a computing article.

16. The apparatus of claim 15, wherein the computer programming product is configured for additional configuration by an end user.

17. The apparatus of claim 16, wherein the computer programming product is capable of being configured to filter raw data collected by the apparatus, identify areas of artifact, and provide signal spectrum composition.

18. The apparatus of claim 17, wherein the computer programming product is capable of being further configured to identify a human subject's neural activity condition.

19. A method to measure electroencephalography, comprising:
   providing an apparatus comprising:
   a flexible, inextensible ribbon with two ends having at least one signal electrode, a reference electrode, a common electrode, at least one battery, at least one electronic block, and multiple eyelets along the length of the ribbon;
   a stretchable, elastic band mounted along the length of the ribbon through the multiple eyelets; and
   a detachable clasp configured to connect the two ends of the flexible ribbon;
   wherein the at least one electronic block is configured to collect bio-signals from the at least one signal electrode and electronically communicate collected bio-signals with an outside computing means,
   wherein the ribbon is divided into multiple segments along the length of the ribbon, the segments being physically and operatively connected to each other,
   wherein each of the at least one battery and at least one electronic block is each located on a separate segment of the ribbon,
   wherein the at least one signal electrode, the reference electrode, and the common electrode are located on one side of the ribbon while the multiple eyelets are on the other side of the ribbon, wherein each of the segments is connected to another segment by a connecting mechanism and the connecting mechanism is detachable from the segments, wherein the common electrode is split into two parts, and the reference electrode is situated between the two parts of the common electrode, wherein the two-part common electrode and the reference electrode are situated on a reference segment, and wherein the reference segment has silicone molding on the inside surface to fit the curve of the forehead;

providing a power source to the apparatus;

placing the apparatus onto a human subject's head such that the segment having the common electrode and the reference electrode comes into physical contact with the human subject's forehead;

providing an outside computing device, the outside computing device having an interface and a computer programming product configured to operatively connect to the apparatus;

tightening the stretchable, elastic band using the clasp to secure the apparatus on the human subject's head;

activating the apparatus using the outside computing device; and collecting bio-signals from the human subject using the outside computing device interface.

20. The method of claim 19, further comprising analyzing the collected bio-signal using the computer programming product and outputting at least one output.

\* \* \* \* \*